(12) United States Patent  (10) Patent No.: US 8,585,697 B2
Wang et al.  (45) Date of Patent: *Nov. 19, 2013

(54) IRRIGATED ABLATION CATHETER ASSEMBLY HAVING A FLOW MEMBER TO CREATE PARALLEL EXTERNAL FLOW

(75) Inventors: Huisun Wang, Maple Grove, MN (US); Christopher J. Geurkink, Minnetonka, MN (US); Harry Puryear, Shoreview, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/615,125

(22) Filed: Sep. 13, 2012

(65) Prior Publication Data

US 2013/0072929 A1  Mar. 21, 2013

Related U.S. Application Data

(63) Continuation of application No. 11/962,623, filed on Dec. 21, 2007, now Pat. No. 8,273,082.

(51) Int. Cl.
*A61B 18/14* (2006.01)

(52) U.S. Cl.
USPC .............................. 606/41; 604/247

(58) Field of Classification Search
USPC .......................... 606/41; 604/247
See application file for complete search history.

(56) References Cited

U.S. PATENT DOCUMENTS

| 5,056,517 | A | 10/1991 | Fenici |
| 5,230,349 | A | 7/1993 | Langberg |
| 5,290,263 | A | 3/1994 | Wigness et al. |
| 5,334,193 | A | 8/1994 | Nardella et al. |
| 5,348,554 | A | 9/1994 | Imran et al. |
| 5,423,811 | A | 6/1995 | Imran et al. |
| 5,462,521 | A | 10/1995 | Brucker et al. |
| 5,545,161 | A | 8/1996 | Imran |
| 5,643,197 | A | 7/1997 | Brucker et al. |
| 5,658,278 | A | 8/1997 | Imran et al. |

(Continued)

FOREIGN PATENT DOCUMENTS

| EP | 1803407 | 7/2007 |
| WO | WO-2005/048858 | 6/2005 |

OTHER PUBLICATIONS

"Supplementary European Search Report", *EP 08864776* Oct. 24, 2011.

(Continued)

*Primary Examiner* — Lee S Cohen
(74) *Attorney, Agent, or Firm* — Dykema Gossett PLLC (57) ABSTRACT

Irrigated ablation catheter assemblies and methods of facilitating parallel irrigation fluid flow along irrigated assemblies includes a catheter, an irrigated ablation electrode assembly, a flow member, and a catheter shaft having a fluid lumen. The electrode assembly includes at least one irrigation passageway and a distal portion. The proximal portion can include a proximal member and the distal portion can include a distal member which is connected to the proximal member. The proximal end of the flow member couples to the catheter shaft and the distal end of the flow member is disposed about the proximal portion of the assembly. Fluid flow is guided at least in part by the member and traverses the outer surface of the proximal portion along the outer surface of the distal portion substantially parallel with the longitudinal axis of the electrode assembly.

20 Claims, 5 Drawing Sheets

(56) References Cited

U.S. PATENT DOCUMENTS

| | | |
|---|---|---|
| 5,697,927 A | 12/1997 | Imran et al. |
| 5,792,140 A | 8/1998 | Tu et al. |
| 5,843,152 A | 12/1998 | Tu et al. |
| 5,893,884 A | 4/1999 | Tu |
| 5,913,856 A | 6/1999 | Chia et al. |
| 5,919,188 A | 7/1999 | Shearon et al. |
| 6,010,500 A | 1/2000 | Sherman et al. |
| 6,015,407 A | 1/2000 | Rieb et al. |
| 6,017,338 A | 1/2000 | Brucker et al. |
| 6,120,476 A | 9/2000 | Fung et al. |
| 6,171,275 B1 | 1/2001 | Webster, Jr. |
| 6,217,576 B1 | 4/2001 | Tu et al. |
| 6,602,242 B1 | 8/2003 | Fung et al. |
| 6,611,699 B2 | 8/2003 | Messing |
| 6,942,661 B2 | 9/2005 | Swanson et al. |
| 7,166,105 B2 | 1/2007 | Mulier et al. |
| 8,273,082 B2 * | 9/2012 | Wang et al. .................. 606/41 |
| 2005/0177151 A1 | 8/2005 | Coen et al. |
| 2006/0184165 A1 | 8/2006 | Webster et al. |
| 2007/0156131 A1 | 7/2007 | Datta |
| 2007/0270791 A1 | 11/2007 | Wang et al. |
| 2008/0071267 A1 | 3/2008 | Wang et al. |
| 2010/0152727 A1 | 6/2010 | Gibson |

OTHER PUBLICATIONS

Thomas, Stuart P. et al., "A comparison of open irrigated and non-irrigated tip catheter ablation for pulmonary vein isolation", *Europace, European Society of Cardiology*, No. 6 2004, 330-335.

Wittkampf, Fred H., "Radiofrequency ablation with a cooled porous electrode catheter", *JACC vol. II*, No. 2; 17a Feb. 1988.

Wittkampf, Fred et al., "Saline-Irrigated Radiofrequency ablation electrode with external cooling", *Journal of Cardiovascular Electrophysiology*, vol. 16, No. 3 Mar. 2005.

* cited by examiner

FIG.7

IRRIGATED ABLATION CATHETER ASSEMBLY HAVING A FLOW MEMBER TO CREATE PARALLEL EXTERNAL FLOW

CROSS-REFERENCE TO RELATED APPLICATIONS

This application is a continuation of U.S. application Ser. No. 11/962,623, filed 21 Dec. 2007 (the '623 application), now issued as U.S. Pat. No. 8,273,082. The '623 application is hereby incorporated by reference as though fully set forth herein.

BACKGROUND OF THE INVENTION a. Field of the Invention

The present invention generally relates to ablation electrodes and/or catheter assemblies having a mechanism for irrigating targeted areas. The present invention further relates to irrigated catheter assemblies that allow for a parallel irrigation flow path through the incorporation of a flow guide or member on the outer surface of the electrode assembly.

b. Background Art

Electrophysiology catheters have been used for an ever-growing number of procedures. For example, catheters have been used for diagnostic, therapeutic, and ablative procedures, to name just a few examples. Typically, a catheter is manipulated through a patient's vasculature to an intended site, for example, a site within the patient's heart, and carries one or more electrodes, which may be used for ablation, diagnosis, or other treatments.

There are a number of methods used for ablation of desired areas including, for example, radiofrequency (RF) ablation. RF ablation is accomplished by transmission of radiofrequency energy to a desired target area through an electrode assembly to ablate tissue at a target site. Because RF ablation may generate significant heat, which if not controlled can result in undesired or excessive tissue damage, such as steam pop, tissue charring, and the like, it is commonly desirable to include a mechanism to irrigate the target area and the device with biocompatible fluids, such as a saline solution. The use of irrigated ablation catheters can also prevent the formation of soft thrombus and/or blood coagulation.

Typically, there are two general classes of irrigated electrode catheters, i.e., open irrigation catheters and closed irrigation catheters. Closed ablation catheters usually circulate a cooling fluid within the inner cavity of the electrode. Open ablation catheters typically deliver the cooling fluid through open outlets or openings on or about an outer surface of the electrode. Open ablation catheters often use the inner cavity of the electrode, or distal member, as a manifold to distribute saline solution, or other irrigation fluids known to those skilled in the art, to one or more passageways that lead to openings/outlets provided on the surface of the electrode. The saline thus flows directly through the outlets of the passageways onto or about the distal electrode member. This direct flow of fluid through the electrode tip lowers the temperature of the tip during operation, rendering accurate monitoring and control of the ablative process more difficult. Accordingly, it is desirable to have a method that allows for cooling of the electrode while providing accurate monitoring and control of the ablative process.

Even for electrode assemblies that are designed with the incorporation of irrigation passageways, if an electrode has a longer length (i.e., for example, over 3 mm), there may be an increased likelihood of developing thrombus caused by protein aggregation and blood coagulation at the tip of the electrode since the standard angled irrigation flow is directed away from the electrode tip and does not reach the longer tip portion or the more distal regions of the electrode due to it length. Moreover, as the length of the electrode increases, the angled fluid passageways provided by an electrode assembly, may be less effective if too much fluid is directed away from the electrode instead of along the body of the electrode to effectively cool the electrode and provide adequate irrigation to prevent the development of thrombus at the distal area of the electrode. Further, for some applications, open flush irrigated ablation catheters with parallel flow may improve the safety of RF catheter ablation by preventing or mitigating protein aggregation and blood coagulation on the surface of the electrode.

BRIEF SUMMARY OF THE INVENTION

The present invention relates to ablation electrode assemblies. The present invention further relates to an irrigated ablation electrode assembly that includes a flow guide or member for creating parallel irrigation flow along the distal member, i.e. ablation electrode, of the electrode assembly.

The present invention also relates to an irrigated ablation catheter assembly. The irrigated catheter assembly includes a catheter, an irrigated ablation electrode assembly, and a flow member. The catheter includes a catheter shaft having a fluid lumen. The irrigated ablation electrode assembly includes a proximal member and a distal member. The proximal member of the electrode assembly further includes a body portion including an outer surface, an inner cavity within the outer body portion, and at least one passageway that extends from the inner cavity to the outer surface of the body portion. The distal member of the electrode assembly further includes a distal end. The flow member of the catheter assembly has a body that includes a proximal end and a distal end. The body of the flow member may be tubular. The proximal end of the flow member is coupled or connected to the catheter shaft and the distal member of the flow member is disposed about the proximal member of the electrode assembly. Accordingly, fluid flows through the irrigated electrode assembly and is guided along the outer surface of the proximal member by the flow member towards the distal member along the outer surface of the distal member substantially parallel with the longitudinal axis of the electrode assembly.

The present invention further provides a method for creating parallel fluid flow along an irrigated electrode assembly. The method includes positioning a fluid member having a body including a proximal end and a distal end about a catheter shaft and proximal member of an irrigated electrode assembly. The body of the flow member may be tubular. The proximal end of the tubular body is connected to the catheter shaft and the proximal end of the body is disposed about an outer surface of the proximal member of the irrigated electrode assembly. The method further includes delivering a fluid to an inner cavity of the proximal member and to at least one passageway that extends from the inner cavity of the proximal member to the outer surface of the proximal member. The fluid flows between the outer surface of the proximal member and the fluid guide towards a distal member of the irrigated electrode assembly substantially in parallel with the longitudinal axis of the electrode assembly.

The present invention further relates to an ablation catheter system including an irrigated ablation electrode assembly connected to a catheter shaft having a flow member connected to or coupled with the catheter shaft and the electrode assembly, therein forming an irrigated catheter assembly connected to an energy source and a fluid source.

The foregoing and other aspects, features, details, utilities, and advantages of the present invention will be apparent from reading the following description and claims, and from reviewing the accompanying drawings.

DETAILED DESCRIPTION OF THE INVENTION

In general, the instant invention relates to irrigated ablation electrode assemblies and methods of using the irrigated ablation electrode assemblies in connection with catheter assemblies. For purposes of this description, similar aspects among the various embodiments described herein will be referred to by the same reference number. As will be appreciated, however, the structure of the various aspects may differ among various embodiments.

Figure 1:
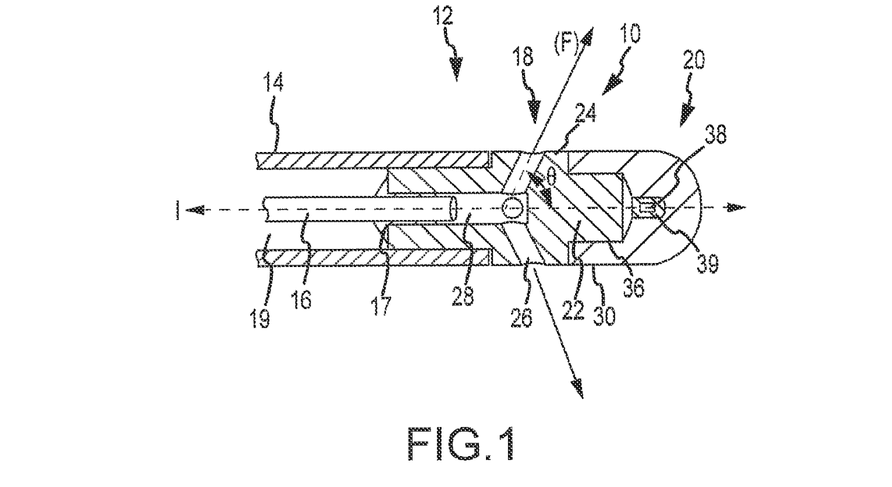
FIG. 1 is a cross-sectional view of an irrigated ablation catheter assembly in accordance with an embodiment of the present invention.

As generally shown in the embodiment illustrated in FIG. 1, the ablation electrode assembly 10 may comprise part of an irrigated ablation catheter assembly 12. Embodiment of the invention describe RF ablation irrigated catheter assemblies; however, the invention may be equally compatible with and applicable to a number of other types of ablation electrodes and catheter assemblies where the temperature of the device and the targeted tissue area may be factors associated with a therapeutic procedure. FIGS. 2 through 7, discussed in more detail, illustrate irrigated catheter assemblies 12 and related components according to alternate embodiments of the present invention.

FIG. 1 is an isometric view of an irrigated ablation electrode assembly 10 connected to a catheter shaft 14 as part of irrigated ablation catheter assembly 12 in accordance with an embodiment of the invention. Catheter assembly 12 includes at least one fluid delivery tube 16 for supplying fluid to electrode assembly 10. Fluid delivery tube 16 may be disposed within a lumen 19 included within catheter shaft 14. Lumen 19 may be a passageway for receiving fluid delivery tube 16, which transport fluid, such as a saline solution, or alternatively fluid may be provided directly through lumen 19 for supplying the irrigated electrode assembly 10. FIG. 1 generally illustrates an irrigated ablation catheter assembly 12 of the type that may be provided by and/or used in connection with the present invention.

As generally illustrated in FIG. 1, electrode assembly 10 may include a proximal member 18 (also referred to as an irrigation member or manifold) and a distal member 20 (also referred to as an ablation electrode member). Proximal member 18 and distal member 20 can be configured for connection together. The orientation of members 18, 20 are generally such that distal member 20, which provides an ablation electrode or an ablative surface, may be provided or situated at or about the distal end of assembly 10. Proximal member 18 may also be referred to as a "proximal portion." Similarly, distal member 20 may also be referred to as a "distal portion." For some embodiments, electrode assembly 10 may be designed and configured to comprise a single unitary electrode assembly 10 that includes a proximal portion and a distal portion. In other embodiments, electrode assembly may comprise a multi-component electrode assembly 10 having separately-formed proximal and distal portions.

Proximal member 18 (i.e., irrigation member) may be provided or located at the proximal end of electrode assembly 10. However, for some embodiments, the orientation could be reversed. Proximal member 18 includes a body portion 22 having an outer surface 24. Proximal member 18 further includes at least one fluid or irrigation passageway 26 (also referred to as proximal passageway 26) that extends from an inner cavity 28, which is disposed within body portion 22, to an orifice or outlet provided by outer surface 24 of proximal member 18. In an embodiment, proximal passageway 26 is separated from and does not come in contact with distal member 20. Inner cavity 28 is generally configured for fluid communication with fluid delivery tube 16. Fluid delivery tube 16 may be securely provided in fluid communication with inner cavity 28 through the coupling to or connection with a seal member 17, which may for example be provided about tube 16 and inserted within inner cavity 28.

Proximal member 18 may include a plurality of passageways 26 that are configured to provide for the flow of fluid through proximal member 18 to outer surface 24 of proximal member 18, and moreover to electrode assembly 10. In an embodiment, inner cavity 28 may serve or act as a manifold or distributor for transporting and/or distributing fluid throughout portions of electrode assembly 10. For example, proximal member 18 may be configured to receive a fluid delivery tube 16 carried within at least a portion of catheter shaft 14. Proximal member 18 may serve as a manifold or distributor of fluid to electrode assembly 10 through passageways 26. Proximal passageways 26 may extend from inner cavity 28 radially outward at an acute angle toward outer surface 24 of proximal member 18. In an embodiment, a plurality of passageways 26 are substantially equally distributed around the circumference of proximal member 18 to provide substantially equal distribution of fluid to the targeted tissue area and/or the outside of electrode assembly 10. If desired, electrode assembly 10 may be configured to provide a single, annular passageway 26, or a number of individual passageways 26 that may be equally distributed around at least a portion of the outer surface 24 of the proximal member 18. Passageways 26 extend to an orifice or outlet provided by outer surface 24. Moreover, the passageways 26 may be generally tubular and may have a substantially constant diameter along the length of the passageway. Alternate configurations of passageways 26 having various diameters along all or portions of the length of the passageways may also be provided.

As shown in FIG. 1, irrigation passageways 26 may be directed towards or extend towards distal member 20 of electrode assembly 10. In an embodiment, passageways 26 extend from the inner cavity 28 of proximal member 18 towards distal member 20 such that a line extending substantially through the center of the passageway 26 forms an acute angle with a longitudinal axis (l) of electrode assembly 10. In an embodiment, irrigation passageways 26 may be directed towards or extend towards distal member 20 at an angle (Θ) equal or less than 90 degrees from the central longitudinal axis of proximal member 18. In an embodiment, passageway 26 extends at an angle (Θ) between about 45 to about 90 degrees. Alternate positions and angles of the passageway(s) 26 may be provided in alternate embodiments of electrode assembly 10.

Based on the angled position of irrigation passageways 26, e.g., as generally illustrated in FIG. 1, the flow of fluid exiting proximal member 18 may have limited contact with distal member 20. In particular, as distal member 20 is increased in length, such as ranging from approximately 3 millimeters to 8 millimeters compared to a 2.5 millimeter distal member, the flow of irrigation fluid, as generally depicted by arrows (F), may be directed away from distal member 20 and limited contact may occur between the irrigation fluid and distal member 20. Accordingly, it can be desirable to provide a more parallel fluid flow, wherein the fluid (F) has a more substantial flow along the outer surface 30 of distal member 20.

Distal member 20, is generally comprised of an electrically, and potentially thermally, conductive material known to those of ordinary skill in the art for delivery of ablative energy to target tissue areas, and may therein provide an ablation electrode. Examples of electrically conductive material include gold, platinum, iridium, palladium, stainless steel, and various mixtures and combinations thereof. In an embodiment, the distal member may provide a distal end 32 that may be rounded (e.g., partially spherical or hemispherical), although other configurations may be used. Distal member 20 may further include a thermal sensor 38, which may be disposed within a thermal cavity 39. Thermal sensor 38 may be disposed along the central longitudinal axis of distal member 20. Such a positioning of thermal sensor 38 may further enhance the temperature sensing properties or capabilities of electrode assembly 10. Thermal sensor 38 can be any mechanism known to one of skill in the art, including for example, thermocouples or thermistors. The temperature sensor 38 may further be substantially surrounded, or at least partially encapsulated, by a thermally conductive and electrically non-conductive material. This thermally conductive and electrically non-conductive material can serve to hold temperature sensor 38 in place within distal member 20 and provide improved heat exchange between temperature sensor 38 and distal member 20. This material may be comprised of a number of materials known to one of ordinary skill in the art, including for example, thermally conductive resins, epoxies, or potting compounds.

Proximal member 18 is comprised of a thermally nonconductive or reduced (i.e. poor) thermally conductive material that serves to insulate the fluid from the remaining portions of electrode assembly 10, for example, distal member 20. Moreover, proximal member 18 may comprise an electrically nonconductive material. Comparatively, proximal member 18 may have lower thermal conductivity than distal member 20. In an embodiment, proximal member 18 may comprise a reduced thermally conductive polymer. A reduced thermally conductive material is one with physical attributes that decrease heat transfer by about 10% or more, provided that the remaining structural components are selected with the appropriate characteristics and sensitivities to maintain adequate monitoring and control of the process. Moreover, a reduced thermally conductive material may include polyether ether ketone ("PEEK"). Further examples of reduced thermally conductive materials that may be useful in conjunction with the present invention include, but are not limited to, high-density polytheylene, polyimides, polyaryletherketones, polyetheretherketones, polyurethane, polypropylene, oriented polypropylene, polyethylene, crystallized polyethylene terephthalate, polyethylene terephthalate, polyester, polyetherimide, acetyl, ceramics, and various combinations thereof. Moreover, for some embodiments, proximal member 18 may be substantially less thermally conductive than distal member 20. As a result, the irrigation fluid flowing through proximal member 18 may have very little thermal effect on distal member 20 due to the poor thermal conductivity of proximal member 18 (e.g. less than 5% effect), and preferably may have nearly 0% effect.

The proximal member 18 may further be configured to include a coupling portion 34 that extends into inner cavity 36 of distal member 20. Proximal member 18 may be generally cylindrical in shape. Moreover, for some embodiments, distal member 20 of ablation electrode assembly 10 may have a generally cylindrical shape terminating in a hemispherical distal end 32. The cylindrical shape of proximal member 18 and distal member 20 may be substantially similar to one another and generally have the same overall diameter, which can provide or create a flush or substantially smooth outer body or profile for electrode assembly 10. Distal member 20 may be configured to accept portion 34 of proximal member 18 for attachment thereto. The distal member 20 may be connected by various known mechanisms, including adhesives, press-fit configurations, snap-fit configurations, threaded configurations, or various other mechanism known to persons of ordinary skill in the art.

Figure 2:
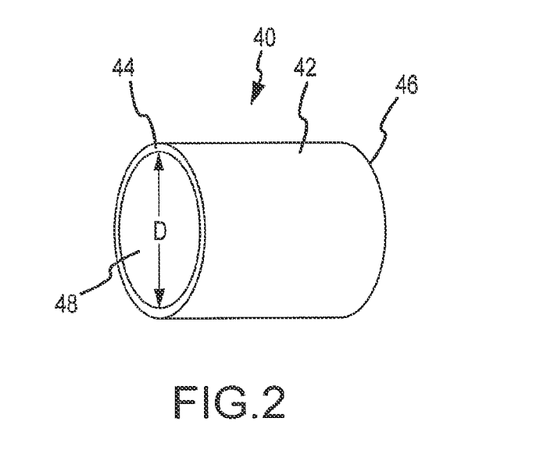
FIG. 2 is an isometric view of a flow member in accordance with an embodiment of the present invention.
Figure 3A:
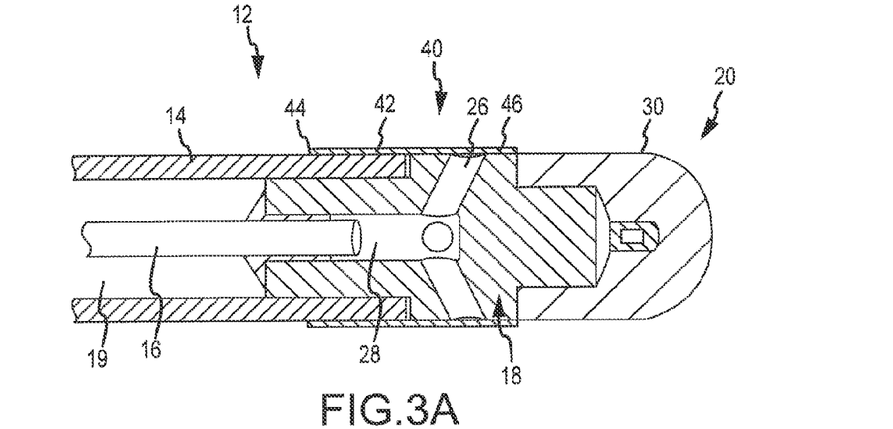
FIG. 3A is a cross-sectional view of an irrigated ablation catheter assembly in accordance with an embodiment of the present invention.
Figure 3B:
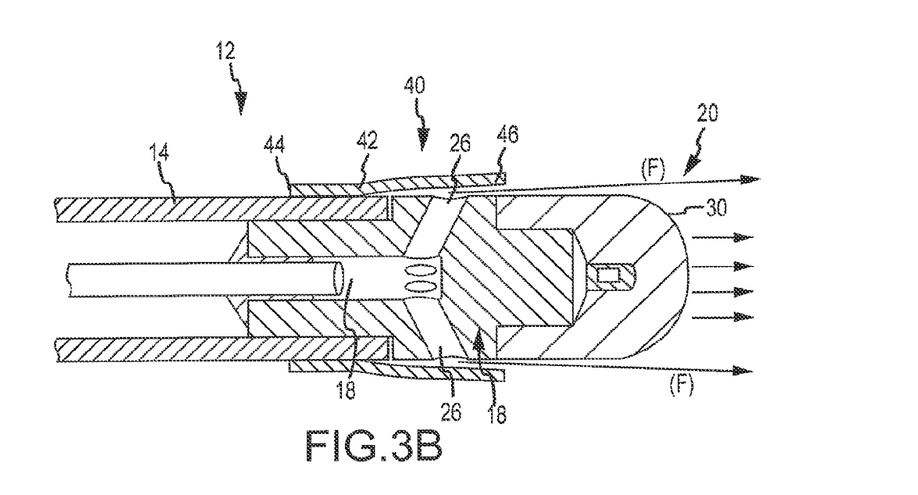
FIG. 3B is an illustrative cross-sectional view of the irrigated ablation catheter assembly as shown in FIG. 2A.

To help guide or direct the flow of fluid about and along the outer surface 30 of distal member 20 of electrode assembly 10, a flow member 40, for example as generally illustrated in FIG. 2, may be coupled or connected to catheter assembly 12. Flow member 40 may be generally cylindrical in shape. In an embodiment, flow member 40 may include a body 42 that may partially surround the outer surface 24 of proximal member 18. In an embodiment, flow member 40, as seen in FIG. 2, may include a tubular body 42 having a proximal end 44 and a distal end 46. Tubular body 42 may include a flow member lumen 48 that receives at least a portion of catheter assembly 12, for example as generally illustrated in FIGS. 3A and 3B. In an embodiment, the body 42 associated with flow member 40 may have a wall thickness of approximately 0.001 inches to approximately 0.005 inches. In an embodiment, flow member 40 may be comprised of a polymer or polymeric material, for example, tubing, and may include various types of polymer tubing known by those of ordinary skill in the art that are suitable for the intended application and treatment environment. In an embodiment, flow member 40 may be comprised of polymer tubing, selected from PEBAX®, polyurethane and mixtures thereof. Further, in an embodiment, flow member 40 may have a substantially constant inner diameter (D). Moreover, in an embodiment, the inner diameter of flow member 40 may be slightly greater than the outer diameter of catheter assembly 12, such that catheter assembly 12 may be attached within flow member 40 and positioned such that flow member 40 is securely attached to catheter assembly 12 at a desired position or location. In another embodiment, flow member 40 may be elastic, having adequate flexibility, to therein permit flow member 40 to stretch to allow fluid flow towards distal member 20. Accordingly, flow member 40 may be comprised of a substantially elastic material, such as those recognized by persons of ordinary skill in the art.

As generally illustrated in FIG. 3A, flow member 40 may be securely attached in connection with catheter assembly 12, including as previously described. In an embodiment, proximal end 44 of flow member 40 may be securely coupled or connected to catheter shaft 14 of catheter assembly 12. Various connections, coupling mechanisms, or means for coupling may be used for sufficiently securing proximal end 44 to catheter shaft 14. Such mechanisms include, but are not limited to, adhesives, bonding (e.g., through heating), pressure, mechanical force, or other mechanism known by those of ordinary skill in the art. As illustrated in FIG. 3B, once fluid is delivered through fluid delivery tube 16 into inner cavity 28 and through passageways 26 of proximal member 18, the fluid may exit passageways 26 and be guided by flow member 40 towards distal member 20 about and along outer surface 30. Accordingly, body 42 directs the fluid flow in a direction substantially parallel with outer surface 30 of distal member 20. In an embodiment, flow member 40 may further be provided to prevent the backflow of blood into catheter assembly 12.

Figure 4:
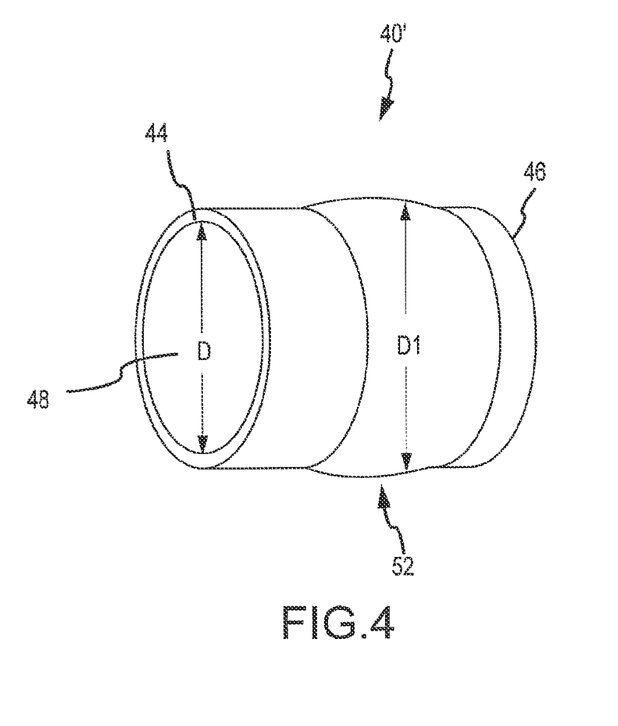
FIG. 4 is an isometric view of a flow member in accordance with an embodiment of the present invention.
Figure 5A:
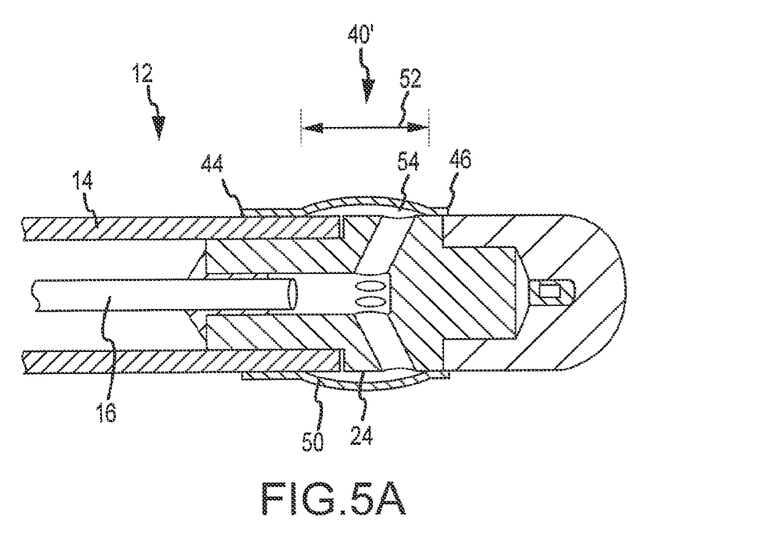
FIG. 5A is a cross-sectional view of an irrigated ablation catheter assembly in accordance with an embodiment of the present invention.
Figure 5B:
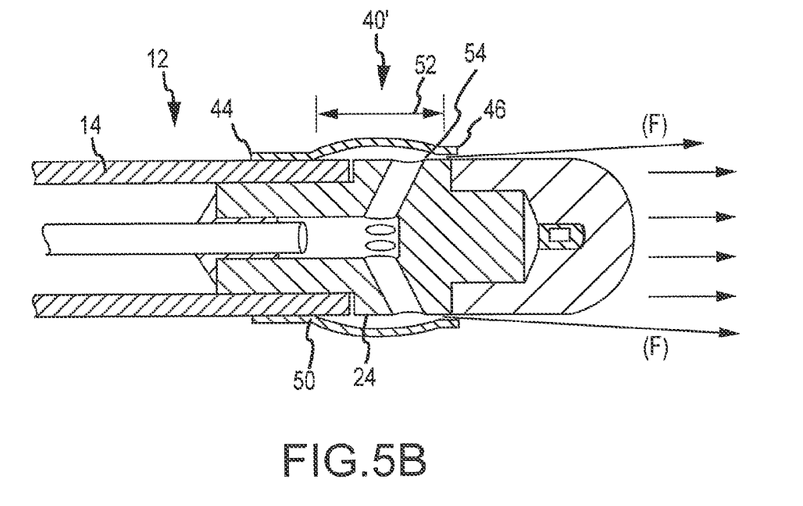
FIG. 5B is an illustrative cross-sectional view of the irrigated ablation catheter assembly as shown in FIG. 3A.

In an embodiment, for example as generally shown in FIG. 4, flow member 40' may include a preformed body 50 having an expanded portion 52 that is provided between proximal end 44 and distal end 46. Expanded portion 52 may have an inner diameter (D1) that is perceptively, or even substantially, greater than the inner diameter (D) of proximal end 44 and distal end 46 of flow member 40'. As further generally illustrated in FIGS. 5A and 5B, upon the insertion of catheter shaft 14 having electrode assembly 10 within flow member lumen 48 of flow member 40', a circumferential space 54 may generally be provided between outer surface 24 of proximal member 18 and preformed body 50 of flow member 40'. Expanded portion 52 enables evenly distributed fluid flow between outer surface 24 of proximal member 18 and preformed body 50 of flow member 40'. Accordingly, flow member 40' may be more readily displaced upon the flow of fluid from passageways 26 and allow for the parallel flow of fluid along outer surface 30 of distal member 20. In an embodiment, distal end 46 of flow member 40' may be elastic and can move radially towards and away from proximal member 18 upon the flow of fluid through distal end 46. Accordingly, distal end 46 of flow members 40 and 40' may be elastic and can move radially towards and away from electrode assembly 10 to facilitate parallel fluid flow along electrode assembly 10 towards distal member 20.

Figure 6:
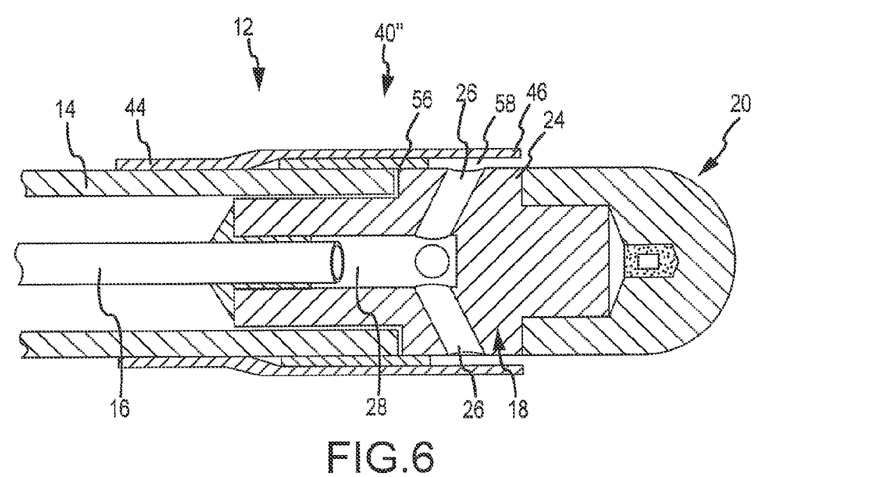
FIG. 6 is a cross-sectional view of an irrigated ablation catheter assembly in accordance with an embodiment of the present invention.

FIG. 6 further illustrates an alternate embodiment, wherein flow member 40" includes a support member 56 disposed between flow member 40" and outer surface 24 of proximal member 18 as well as catheter shaft 14. Support member 56 may be positioned relative to proximal member 18 such that support member 52 is disposed proximally to passageways 26. Circumferential space 58 is provided between outer surface 24 of proximal member 18 and distal end 46 of flow member 40". Proximal end 44 of flow member 40" has a diameter less than distal end 46 of flow member 40". In an embodiment, the diameter of distal end 46 may be substantially equal to the diameter of proximal end 44 plus the thickness of support member 56. The design of flow members 40, 40' and 40" may vary depending on the types of materials used and/or various structural alternations made during the manufacturing process intended to facilitate parallel irrigation flow along electrode assembly 10.

Figure 7:
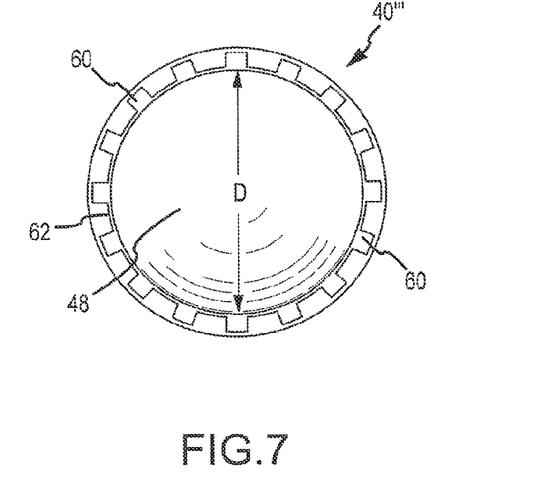
FIG. 7 is a end view of a flow member in accordance with an embodiment of the present invention.

FIG. 7 illustrates an additional embodiment of the present invention, wherein flow member 40''' further includes a plurality of axial passageways 60 that are provided along the inner surface 62 of body 64 of flow member 40'''. Flow member 40'''' further includes a flow member lumen 48 for receiving catheter shaft 14 and electrode assembly 10. Axial passageways 60 may be equally disposed circumferentially about all or a portion of the inner surface 62 of body 64. Moreover, axial passageways 60 may extend along a portion of inner surface 62 to distal end 46 of flow member 40'''. Axial passageways 60 provide fluid channels for the fluid to flow through to further allow for parallel irrigation fluid flow about and along electrode assembly 10, including in parallel with distal member 20.

Although a number of embodiments of this invention have been described above with a certain degree of particularity, those skilled in the art could make numerous alterations to the disclosed embodiments without departing from the spirit or scope of this invention. Other embodiments and uses of the devices and method of the present invention will be apparent to those skilled in the art from consideration of the specification and practice of the invention disclosed therein.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An irrigated ablation catheter assembly comprising:
   a catheter shaft comprising a lumen;
   an irrigated ablation electrode assembly comprising a body including an outer surface, an inner cavity, and a passageway that extends from the inner cavity to the outer surface of the body; and
   a flow member comprising a body including a proximal end and a distal end and a longitudinal axis extending from the proximal end to the distal end, wherein the flow member is disposed so as to overlay an outlet for the passageway,
   further wherein the body of the flow member comprises at least one of a transverse cross-section that varies between the proximal end and the distal end of the flow member body and a longitudinal cross-section that varies about the circumference of the flow member body.

2. The irrigated ablation catheter assembly of claim 1, wherein the longitudinal cross-section of the flow member body varies according to a varying wall thickness of the flow member body.

3. The irrigated ablation catheter assembly of claim 1, wherein the transverse cross-section of the flow member body varies according to a varying inner radius of the flow member body.

4. An irrigated ablation catheter comprising:
   a catheter shaft comprising a lumen;
   an irrigated ablation electrode assembly comprising a body including an outer surface comprising an outlet, an inner cavity, and a passageway that extends from the inner cavity to the outlet; and
   a flow member disposed so as to overlay the outlet, the flow member comprising a body including a proximal end and a distal end and a longitudinal axis extending from the proximal end to the distal end, wherein, when fluid is not flowing through the outlet, the body of the flow member comprises at least one of a transverse cross-section that varies between the proximal end and the distal end of the flow member body and a longitudinal cross-section that varies about the circumference of the flow member body.

5. The irrigated ablation catheter of claim 4, wherein the flow member comprises an elastic material.

6. The irrigated ablation catheter of claim 5, wherein the flow member is configured to stretch to allow fluid flow to a distal portion of the irrigated ablation electrode assembly.

7. The irrigated ablation catheter of claim 5, wherein the flow member is configured to move radially towards and away from a proximal portion of the irrigated ablation electrode assembly.

8. The irrigated ablation catheter of claim 7, wherein the flow member is configured to move radially upon a flow of fluid through the irrigated ablation electrode assembly.

9. The irrigated ablation catheter of claim 5, wherein the passageway comprises one of a plurality of passageways that are evenly distributed circumferentially about an inner surface of the flow member.

10. The irrigated ablation catheter of claim 5, wherein the flow member is comprised of a polymeric material.

11. The irrigated ablation catheter of claim 5, wherein the irrigated ablation electrode assembly comprises a plurality of passageways disposed circumferentially about and extending to the outer surface of the body.

12. The irrigated ablation catheter of claim 4, wherein the flow member is configured to move radially towards and away from a proximal portion of the irrigated ablation electrode.

13. The irrigated ablation catheter of claim 4, wherein the flow member is configured to move radially upon a flow of fluid through the irrigated ablation electrode assembly.

14. The irrigated ablation catheter of claim 4, wherein an outer surface portion of a distal portion of the irrigated ablation electrode assembly is generally parallel to a longitudinal axis of the irrigated ablation electrode assembly.

15. The irrigated ablation catheter of claim 4, wherein a proximal portion of the irrigated ablation electrode assembly comprises a plurality of passageways disposed circumferentially about and extending to the outer surface.

16. The irrigated ablation catheter of claim 4, wherein a thermal sensor is disposed within the irrigated ablation electrode assembly.

17. The irrigated ablation catheter of claim 4, wherein the flow member further comprises a proximal portion and a distal portion and is configured to take a first configuration and a second configuration and wherein the second configuration comprises a distal end of the flow member being separated radially from a proximal portion of the irrigated ablation electrode assembly.

18. The irrigated ablation catheter of claim 17, wherein the first configuration comprises the distal end of the flow member abutting the proximal portion of the electrode assembly.

19. An irrigated ablation catheter assembly comprising:
a catheter shaft comprising a lumen;
an irrigated ablation electrode assembly comprising a body including an outer surface comprising an outlet, an inner cavity, and a passageway that extends from the inner cavity to the outlet; and
means for overlaying the outlet,
wherein the means for overlaying the outlet comprises at least one of a transverse cross-section that varies between a proximal end and a distal end of the means for overlaying the outlet and a longitudinal cross-section that varies about a circumference of the means for overlaying the outlet.

20. The irrigated ablation catheter of claim 19, wherein the means for overlaying the outlet comprises means for taking a first configuration and a second configuration.

* * * * *